United States Patent [19]

Nafissi-Varchei

[11] 4,406,893

[45] Sep. 27, 1983

[54] N-ALKOXYCARBONYL-N'-[2-NITRO-4 OR 5-ALKYLTHIOPHENYL]-N''-[SUBSTITUTED ALKYL]-GUANIDINES USEFUL AS ANTHELMINTICS

[75] Inventor: M. Mehdi Nafissi-Varchei, North Caldwell, N.J.

[73] Assignee: Schering Corporation, Kenilworth, N.J.

[21] Appl. No.: 346,442

[22] Filed: Feb. 8, 1982

Related U.S. Application Data

[63] Continuation-in-part of Ser. No. 198,424, Oct. 20, 1980, Pat. No. 4,348,406.

[30] Foreign Application Priority Data

Oct. 12, 1981 [EP] European Pat. Off. ........ 81108212.2

[51] Int. Cl.³ .................. A61K 31/36; C07C 149/40; C07C 141/16; C07F 9/02
[52] U.S. Cl. ................ 424/199; 260/458 C; 260/501.14; 260/502.5 E; 260/502.5 G; 260/924; 260/941; 424/211; 424/300; 424/303; 560/9; 560/13; 426/635; 426/532
[58] Field of Search .............. 560/13, 9; 260/458 C, 260/507 R, 501.14, 924, 941, 502.5 E, 502.5 G; 424/300, 303, 199, 211; 426/635

[56] References Cited

U.S. PATENT DOCUMENTS 4,217,358 8/1980 Haugwitz ........................ 560/9
4,246,260 1/1981 Kölling et al. .................. 560/9
4,293,569 10/1981 Haugwitz et al. .............. 560/13

FOREIGN PATENT DOCUMENTS 1576633 10/1980 United Kingdom ............. 560/13

OTHER PUBLICATIONS

Gyurik et al., C.A., 84 31,074r (1976).

Primary Examiner—Nicky Chan
Attorney, Agent, or Firm—Anita W. Magatti; Paul H. Ginsburg; Bruce M. Eisen

[57] ABSTRACT

Compounds of the formula

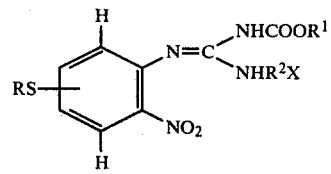

and their pharmaceutically acceptable salts are disclosed. The compounds are useful as anthelmintics.

16 Claims, No Drawings

N-ALKOXYCARBONYL-N'-[2-NITRO-4 OR 5-ALKYLTHIOPHENYL]-N"-[SUBSTITUTED ALKYL]-GUANIDINES USEFUL AS ANTHELMINTICS

This application is a continuation-in-part of copending application Ser. No. 198,424, filed Oct. 20, 1980, now U.S. Pat. No. 4,348,406.

The present invention relates to novel guanidine derivatives. Compounds of the invention are useful as anthelmintics.

Compounds of the present invention may be represented by the formula

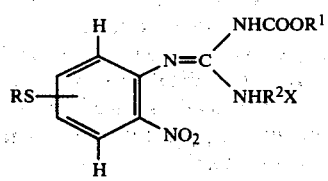

wherein
R and $R_1$ are $C_1$ to $C_6$ alkyl;
$R_2$ is $C_1$ to $C_6$ alkylene;
X is an acid function selected from the group consisting of COOH, $SO_3H$, $OSO_3H$, $PO_3H_2$ and $OPO_3H_2$; and the pharmaceutically acceptable salts thereof.

In the above compounds, the alkyl groups may be linear, branched or cyclic.

The pharmaceutically acceptable salts contemplated include metal salts, e.g. alkali metal salts such as sodium, potassium, and calcium, and other physiologically acceptable salts, e.g. alkyl ammonium salts such as N-methylglucamine, ethanolamine, diethanolamine, triethanolamine, pyridinium and procaine.

Preferred compounds are those wherein R is propyl, $R^1$ is methyl, $R^2$ is methylene or ethylene, and X is COOH or $SO_3H$. Especially preferred are compounds wherein R is propyl, $R^1$ is methyl, $R^2$ is ethylene and X is $SO_3H$. Preferred pharmaceutically acceptable salts are the alkyl ammonium salts.

Also included within the scope of

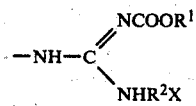

invention are the isomers at the guanidine groups, e.g. t,0030

Examples of compounds of formula I are as follows:
N-methoxycarbonyl-N'-[2-nitro-5-propylthiophenyl]-N"-[2-carboxyethyl]guanidine,
N-methoxycarbonyl-N'-[2-nitro-4-propylthiophenyl]-N"-[2-carboxyethyl]guandine,
N-ethoxycarbonyl-N'-[2-nitro-5-propylthiophenyl]-N"-[2-carboxyethyl]guanidine,
N-methoxycarbonyl-N'-[2-nitro-5-ethylthiophenyl]-N"-[2-carboxyethyl]guanidine,
N-methoxycarbonyl-N'-[2-nitro-4-ethylthiophenyl]-N"-[2-carboxyethyl]guandine,
N-methoxycarbonyl-N'''-[2-nitro-5-butylthiophenyl]-N"-[2-carboxyethyl]guanidine,
N-methoxycarbonyl-N'-[2-nitro-5-propylthiophenyl]-N"-[2-carboxypropyl]guanidine,
N-methoxycarbonyl-N'-[2-nitro-5-propylthiophenyl]-N"-[2-carboxymethyl]guanidine,
N-methoxycarbonyl-N'-[2-nitro-5-propylthiophenyl]-N"-[2-ethyl hydrogen sulfate]guanidine,
N-methoxycarbonyl-N'-[2-nitro-5-propylthiophenyl]-N"-[2-ethyl sulfonic acid]guanidine,
N-methoxycarbonyl-N'-[2-nitro-5-propylthiophenyl]-N"-[2-ethyl hydrogen phosphate]guandine, and
N-methoxycarbonyl-N'-[2-nitro-5-propylthiophenyl]-N"-[2-ethyl phosphoric acid]guanidine.

Of the above, N-methoxycarbonyl-N'-[2-nitro-5-propylthiophenyl]-N"-[2-ethyl sulfonic acid]guanidine is preferred, especially as an alkyl ammonium salt, e.g. the N-methylglucamine salt.

The present invention also relates to methods of preparing compounds of formula I and to the use of the compounds as anthelmentics.

The compounds of this invention may be prepared according to processes generally known in the art for preparing similar compounds. The following reaction scheme illustrates the preparation of the instant compounds:

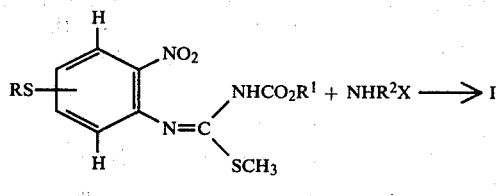

In the above scheme, R, $R^1$, $R^2$ and X are as defined above. The reaction is preferably carried out by dissolving the reactants II and III in an appropriate solvent, e.g. methanol-water, and by stirring the resulting solution, preferably at ambient temperatures, until the reaction is completed. Starting materials II and III are either known or may be prepared by standard reactions known in the art.

The metal salts and alkyl ammonium salts of the acid function X may be prepared according to methods well known to those skilled in the art.

The following Example further illustrates the preparation of the compounds of the instant invention.

EXAMPLE 1

N-Methoxycarbonyl-N-'-[2-Nitro-5-Propylthiophenyl]-N"-[2-Ethyl Sulfonic Acid]Guanidine Sodium Salt A solution of taurine (135.2 g, 1.08 mole) and sodium hydroxide (43.2 g, 1.08 mole) in water (270 ml) was added to a solution of N-methoxycarbonyl-N'-[2-nitro-4-propylthiophenyl]-S-methyl-isothiourea (185.4 g, 0.54 mole) in methanol (3900 ml). After stirring five days, solids were collected by filtration. A second crop of solids was collected after bubbling nitrogen through the filtrate to remove methanethiol and methanol, and a third crop was obtained after allowing the remaining solvent to evaporate. The combined solids were washed with hot chloroform, then dissolved in boiling methanol, and filtered. The filtrate was allowed to crystallize, yielding 105 g purified title compound, m.p. 150° C. (decomposes).

EXAMPLE II

N-Methoxycarbonyl-N'-[2-Nitro-5-Propylthiophenyl]-N''-[2-Ethyl Sulfonic Acid]Guanidine 31.1 g (7 mmoles) of the product of Example I was dissolved in deionized water (60 ml) at room temperature with stirring, and aqueous hydrochloric acid (8.0 ml of a 1.0 N solution) was added in one portion. After stirring for 30 minutes the resultant precipitate was filtered off, washed repeatedly with deionized water and allowed to dry in air to give the title compound, m.p. 215° C. (decomposes).

EXAMPLE III

N-Methoxycarbonyl-N'-[2-Nitro-5-Propylthiophenyl]-N''-[2-Ethyl Sulfonic Acid]Guanidine N-Methyl Glucamine Salt The produce of Example II (4.21 g, 10 mmoles) was added in one portion to a stirred solution of N-methylglucamine (1.95 g, 10 mmoles) in hot methanol (75 ml). After cooling, a yellow solid was filtered off and recrystallized twice from methanol to obtain the title compound, m.p. 17–120° C. (decomposes).

In a similar manner, using the product of Example II and the appropriate reagent, such salts as the ammonium salt, the diethanolamine salt and the Tris(hydroxymethyl)aminomethane salt may be prepared.

EXAMPLE IV

N-Methoxycarbonyl-N'-[2-Nitro-5-Propylthiophenyl]-N''-[2-Ethyl Sulfonic Acid]Guanidine Calcium Salt The product of Example I (6.6 g, 15 mmoles) was dissolved in water (150 ml) and a solution of calcium chloride (3.33 g, 30 mmoles) in water (10 ml) was added rapidly with stirring. After stirring 15 minutes, the precipitate was filtered off, washed with cold water and dried in vacuo overnight at 60° C. to give the title compound, m.p. 300° C.

In a similar manner, using suitable starting materials, prepare the following:

N-methoxycarbonyl-N'-[2-nitro-5-propylthiophenyl]-N''-[2-carboxyethyl]guanidine, m.p. 116°–118° (dec);

N-methoxycarbonyl-N'-[2-nitro-5-propylthiophenyl]-N''-[2-carboxypropyl]guanidine, m.p. 112°–114° (dec);

N-methoxycarbonyl-N'-[2-nitro-5-propylthiophenyl]-N''-2-carboxymethyl]guanidine sodium salt, m.p. 195°–198° (dec); and N-methoxycarbonyl-N'-[2-nitro-5-propylthiophenyl]-N''-[2-ethyl hydrogen sulfate]guanidine sodium salt, m.p. 150° (dec).

The compounds of the present invention are useful in combatting helminths, i.e. in treating animals, including humans, suffering from an infestation of parasitic worms, for example, roundworms, hookworms, whipworms or tapeworms, by administering to the host animal a therapeutic amount of a compound of the present invention.

The compounds of this invention exhibit significant anthelmintic effects when administered to a host (e.g. a human, swine, dog or ruminant) at doses as low as about one milligram per kilogram of body weight per day in dosing over several days, or at about fifty milligrams per kilograms in a single day dosing, according to techniques well known in the art.

The optimum does for each species of animal and for each type of parasite can readily be determined by one skilled in the art of using standard techniques such as the Modified McMaster Egg Counting Technique as described by H. B. Whitlock and H. McL. Gordon, J. Council Scientific Industrial Research (Australia) 12, p. 50, 1939 and H. B. Whitlock, J. Council Scientific Research (Australia) 21, p. 177, 1948.

From these, and similar tests, anthelmintic efficacy is assessed by determining the number of eggs in feces passed on the days following treatment with the compound compared with pretreatment days. In addition, autopsy of animals after treatment will indicate whether the infection has been eradicated. Based on experimentation, proper dosages for curing various infections can be determined.

The compounds of this invention may be administered in suspensions, capsules, feed additive preparations, tablets, etc. as is well known to those skilled in the human and veterinary medical arts. In addition, the compounds may also be used as injectible anthelmintic preparations. For this purpose, the active ingredient is admixed with suitable sterile carriers such as sterile water and isotonic saline solution.

Suitable clinical formulations containing the compounds of this invention can be administered orally in the form of tablets, capsules, elixirs and the like. The active compound is compounded with inert carriers such as, for example, gums, starches and sugars or it may be incorporated into gelatine capsules or formulated into elixirs which have the advantage of being susceptible to manipulations in flavor by the addition of standard, natural or synthetic flavoring agents.

Particularly useful anthelmintic formulations comprising the compounds of this invention for treatment of helminthiasis are either liquid suspensions ready to use or wettable or water-dispersible powders which are mixed with water prior to use.

The following examples show particularly useful formulations. In the examples, the term "Drug" refers to N-methoxycarbonyl-N'-[2-nitro-5-propylthiophenyl]-N''-[2-ethylsulfonic acid]guanidine N-methyl-glucamine salt. It will be appreciated by those skilled in the art that an equivalent amount of another compound of formula I may be substituted for the named compound.

A. Liquid-suspension Formulation

A liquid-suspension formulation may contain from 50 to 55% w./v. (grams/liters) of the active compound together with a dispersing agent and stabilizing agent. A typical formulation is as follows:

Drug—50 to 55 parts by weight
Dispersing agent—½ to 2 parts by weight
Stabilizing agent—1 to 3 parts by weight
Preservative—as required
Water—Sufficient to make 100 volumes.

Suitable dispersing agents are those containing sulphonate groups, for example sodium lignin sulphonate, or the sulphonated phenol or naphthol formaldehyde polymers. Bentonite may be employed as the stabilizing agent, although it is possible to use such protective colloids as carboxymethyl cellulose, sodium alginate and the like. The formulations can be prepared by mixing the active compound and water containing dissolved dispersing agents very vigorously by means of suitable mechanical mixing equipment.

B. Powder Formulation

A wettable or water-dispersible powder formulation may contain about 90 to 95% w./w. of the active compound together with a wetting agent and dispersing agent. A diluent such as kaolin can also be added if a concentration below about 98% w./w. is required. An anti-foaming agent and, in some cases, a stabilizing agent may be present. A typical formulation is as follows:

Drug—90 to 95 parts by weight
Wetting agent—½ to 4 parts by weight
Stabilizing agent—0 to 2 parts by weight
Anti-foaming agent—0.01 to 1 part by weight
Water—0 to 5 parts by weight Suitable wetting agents are the non-ionic alkyl-phenolethylene oxide adducts, such as an octylphenol or nonylphenol condensed with ten moles of ethylene oxide, or anionic materials, such as the synthetic aryl alkyl sulphonates, or sodium dibutyl napthalene sulphonate. In general, about 1% w./w. wetting agent is required. The anti-foaming agent employed may be either a silicone or such materials as ethyl hexanol, octanol and the like; and the stabilizing agent may again be chosen from bentonite or the water-soluble gums. Wettable or water-dispersible powder formulations are prepared by careful and adequate mixing of the active compound with other ingredients with or without the addition of some water using typical powder blending equipment such as a ribbon blender. The powder is stirred into water by the user before application in the field.

| C. Tablet formulation | |
|---|---|
| | Grams per 1000 tablets |
| Drug | 200.0 |
| Lactose | 90.0 |
| Dicalcium phosphate, hydrous | 122.5 |
| Polyvinylpyrolidone | 25.0 |
| Polyethyleneglycol 1500 | 7.5 |
| Corn Starch | 50.0 |
| Magnesium Stearate | 5.0 |
| | 500.0 |

Mix the active compound, the lactose and the diacalcium phosphate. Dissolve the polyethyleneglycol 1500 the polyvinylpyrrolidone in approximately 20 ml of water. Granulate the powder blend with the water solution, adding additional water if necessary, to product a damp mass. Pass the wet granulation through a 12 mesh screen; spread on trays and air dry at 35° C. Blend the dry granulates with the starch and the magnesium stearate. Compress into 500 mg tablets.

| D. Capsule formulation | |
|---|---|
| | Grams per 1000 capsules |
| Drug | 200.0 |
| Lactose | 198.0 |
| Magnesium Stearate | 2.0 |
| | 400.0 |

Blend the ingredients and fill into hard gelatine capsules.

| E. Elixir formulation | |
|---|---|
| | per 1000 ml |
| Drug | 40.0 g |
| Sodium citrate | 10.0 g |
| Sugar | 500.0 g |
| Glycerin | 200.0 g |
| Compound orange spirit | 10.0 ml |
| Alcohol | 100.0 ml |
| Amaranth | 0.1 ml |
| Water to total | 1000.0 ml |

Combine the above ingredients using standard techniques.

| F. Injectible formulation | |
|---|---|
| | mg/ml |
| Drug | 50.0 |
| Polyethylene Glycol 400 | 500.0 |
| Dimethyl Acetamide | 300.0 |
| Benzyl Alcohol | 20.0 |
| Water for Injection to q.s. | 1.0 ml |

Combine the above ingredients using standard techniques.

| G. Injectible formulation | |
|---|---|
| | mg/ml |
| Drug | 100.0 |
| Dimethyl Acetamide | 300.0 |
| Benzyl Alcohol | 20.0 |
| Polyethylene Glycol 400 to q.s. | 1.0 ml |

Combine the above ingredients using standard techniques.

I claim:

1. A compound of the formula $$RS\text{-}C_6H_2(H)(H)(NO_2)\text{-}N=C(NHCOOR^1)(NHR^2X)$$

wherein
R and $R^1$ are $C_1$ to $C_6$ alkyl;
$R_2$ is $C_1$ to $C_6$ alkylene;
X is an acid function selected from the group consisting of COOH, $SO_3H$, $OSO_3H$, $PO_3H_2$ and $OPO_3H_2$; and the pharmaceutically acceptable salts thereof.

2. A compound of claim 1 wherein R is propyl.

3. A compound of claim 1 wherein $R^1$ is methyl.

4. A compound of claim 1 wherein R is propyl, $R^1$ is methyl, and X is COOH or $SO_3H$.

5. A compound of claim 4 which is N-methoxycarbonyl-N'-[2-nitro-5-propylthiophenyl]-N''-[2-ethyl sulfonic acid]guanidine.

6. A compound of claim 4 which is N-methoxycarbonyl-N'-[2-nitro-5-propylthiophenyl]-N''-[2-carboxymethyl]guanidine.

7. A compound of claim 4 which is N-methoxycarbonyl-N'-[2-nitro-5-propylthiophenyl]-N''-[2-carboxyethyl]guanidine.

8. A compound of claim 4 which is N-methoxycarbonyl-N'-[2-nitro-5-propylthiophenyl]-N''-[2-carboxypropyl]guanidine.

9. A compound of claim 1 which is N-methoxycarbonyl-N'-[2-nitro-5-propylthiophenyl]-N''-[2-ethyl hydrogen sulfate]guanidine sodium salt.

10. A pharmaceutically acceptable salt of the compound of claim 5, wherein the pharmaceutically acceptable salt is an alkyl ammonium salt.

11. A compound of claim 10 wherein the alkyl ammonium salt is selected from the group consisting of N-methylglucamine, diethanolamine and triethanolamine.

12. A method of treating helminth infestation in mammals which comprises administering to an infected animal an anthelmintic effective amount of a compound of claim 1.

13. An anthelmintic composition comprising an anthelmintic effective amount of a compound of claim 1 and a pharmaceutically acceptable carrier.

14. An anthelmintic composition in injectable form comprising an anthelmintic effective amount of a compound of claim 1 and a pharmaceutically acceptable carrier.

15. A compound of claim 1 wherein X is $SO_3H$.

16. A compound of claim 4 which is N-methoxycarbonyl-N'-[2-nitro-4-propylthiophenyl]-N''-[2-ethyl sulfonic acid]guanidine.

* * * * *